(12) United States Patent
Tsai

(10) Patent No.: US 6,391,008 B1
(45) Date of Patent: May 21, 2002

(54) SAFETY HYPODERMIC SYRINGE

(76) Inventor: Hsi-Chin Tsai, 2nd Fl., No. 524, Ta-An Rd., Shulin City, Taipei Hsien (TW)

( * ) Notice: Subject to any disclaimer, the term of this patent is extended or adjusted under 35 U.S.C. 154(b) by 135 days.

(21) Appl. No.: 09/638,359

(22) Filed: Aug. 15, 2000

(51) Int. Cl.⁷ .................................................. A61M 5/32
(52) U.S. Cl. ........................ 604/195; 604/110; 604/111
(58) Field of Search ................................. 604/110, 111, 604/192, 195, 263, 162

(56) References Cited

U.S. PATENT DOCUMENTS

| | | | | |
|---|---|---|---|---|
| 5,205,827 A | * | 4/1993 | Novacek et al. | 604/110 |
| 6,066,115 A | * | 5/2000 | Chang Lai | 604/110 |
| 6,093,171 A | * | 7/2000 | Huang | 604/110 |
| 6,102,893 A | * | 8/2000 | Aneas | 604/111 |
| 6,193,687 B1 | * | 2/2001 | Lo | 604/110 |
| 6,193,695 B1 | * | 2/2001 | Rippstein, Jr. | 604/110 |

* cited by examiner

Primary Examiner—Anhtuan T. Nguyen
(74) Attorney, Agent, or Firm—William E. Pelton, Esq.

(57) ABSTRACT

A safety hypodermic syringe includes a barrel, a needle seat airtightly contained in the barrel, an elastic ring contained in the needle seat, a stopper, and a plunger coupled with the stopper. A needle is able to threadedly engage with the needle seat. After an injection treatment, the plunger can be pulled to draw the needle seat, together with the needle engaged therewith, back into the barrel, and can be removed from the stopper for recycling. With the syringe of the invention, the plunger thereof is recyclable, the needle hub thereof is able to be securely installed, the needle thereof is not able to stick out from the barrel thereof, remaining medicine therein after use is less than conventional syringes, and whether it has been used is able to be plainly indicated by a security bar.

4 Claims, 6 Drawing Sheets

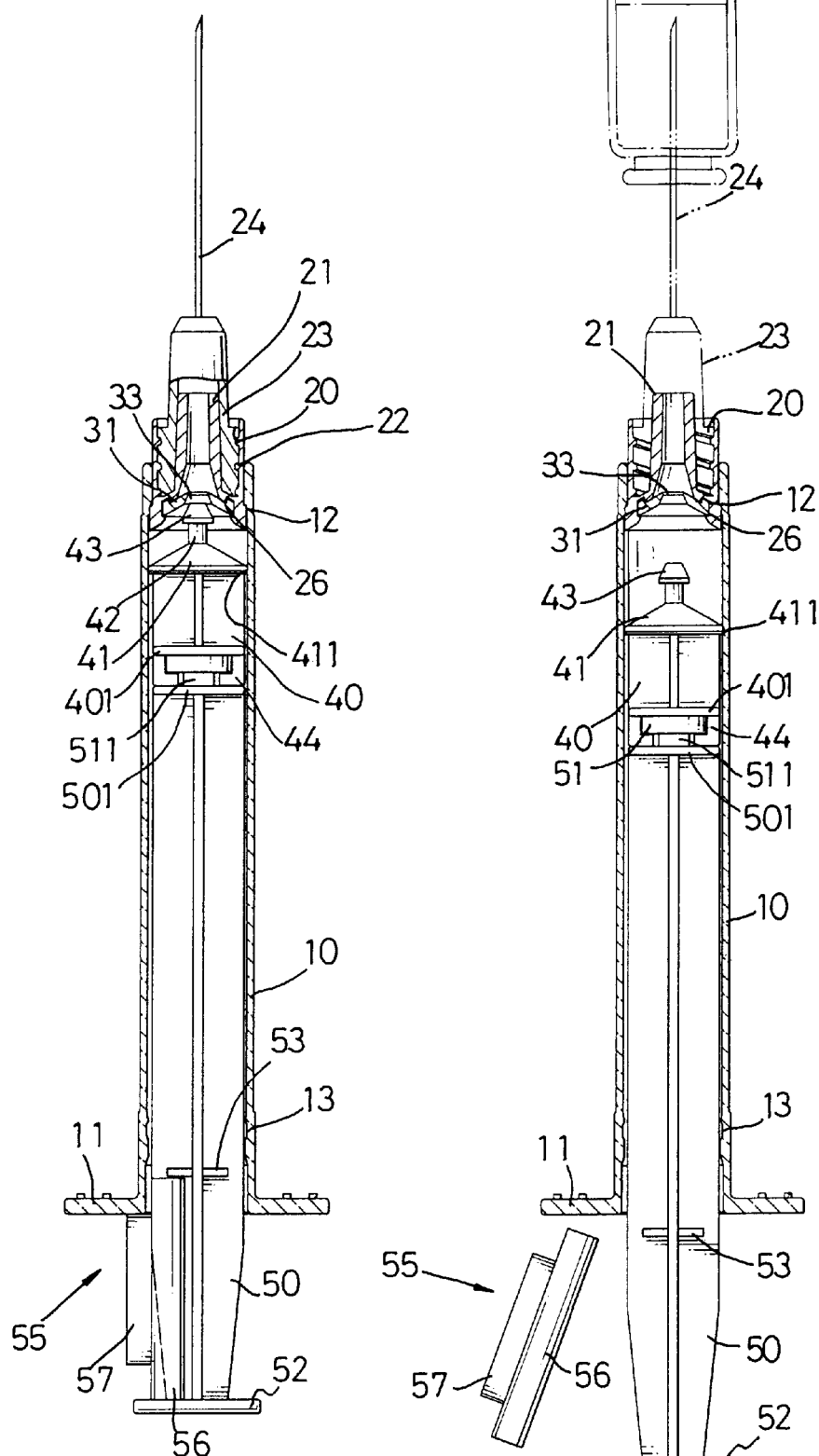

SAFETY HYPODERMIC SYRINGE

BACKGROUND OF THE INVENTION

1. Field of the Invention

The invention relates to a safety hypodermic syringe, especially to a syringe in which a plunger thereof is recyclable, a needle hub thereof is able to be securely installed, a needle thereof need notstick out from a barrel thereof after use, medical liquid contained therein after use is less than conventional syringes, and whether it has been used is able to be clearly indicated by a security bar.

2. Description of Related Art

A hypodermic syringe is a common medical instrument which is used in a large amount every day. Present hypodermic syringes are one-time use type and can be discarded after use. To prevent needles of such used syringes hurting people, safety syringes whose needles can be pulled back into barrels thereof have been provided. One typical type of such safety syringes is as shown in FIG. 9. In the figure, it is seen that the syringe has a barrel (62), a plunger (63) contained in the barrel (62), and a needle hub (60) installed on an upper end (61) of a needle seat contained in a top tube of the barrel (62). A stopper is formed on a top of the plunger (63) and hermetically contacts with an inner surface of the barrel (63). A central pole with an enlarged head is formed on the stopper. At the end of an injection process, the head enters a rear cavity of the seat and engages with a pair of small protrusions (600). Then, by pulling back the plunger (63), the head will drive the seat, and thus the needle installed on the seat, backward into the barrel (62). To indicate whether the syringe has been used, a security cord (64) is provided being formed on a finger flange of the syringe and extending downward to engage with a thumb rest (65) of the syringe. The security cord (64) is so thin that once the plunger (63) is pulled back with respect to the barrel (62) to suck medical liquid into the syringe, it will break to indicate that the syringe has been used.

However, this kind of conventional safety syringe has some drawbacks:

1. in actual use, it is found there is always some medical liquid remaining in the rear cavity thereof and this will cause unnecessary waste;
2. the needle hub (60) stays on the seat just by a certain friction force therebetween and therefore it may fall off from the seat;
3. after use, the plunger (63) cannot be removed from the syringe and this means the plunger (63) is not recyclable;
4. after use and the needle having been pulled back into the barrel (62), there is still the possibility that the plunger (63) is pushed by accident to drive the needle out of the barrel (62) again, which is obviously dangerous; and,
5. the security cord is too thin and may break by accident before the syringe is really used, which may also cause waste.

SUMMARY OF THE INVENTION

The main object of the invention is to provide a safety hypodermic syringe wherein a plunger thereof is recyclable, a needle hub thereof is able to be securely installed, a needle thereof will not stick out from a barrel thereof after use, medical liquid contained therein after use is less than conventional syringes, and whether it has been used is able to be plainly indicated by a security bar.

Other objects, advantages and novel features of the invention will become more apparent from the following detailed description when taken in conjunction with the accompanying drawings.

BRIEF DESCRIPTION OF THE DRAWINGS

FIGS. 2 to 6 are cross sectional views of the embodiment shown in FIG. 1 showing using process of the invention;

DETAILED DESCRIPTION OF THE PREFERRED EMBODIMENTS

Figure 1:
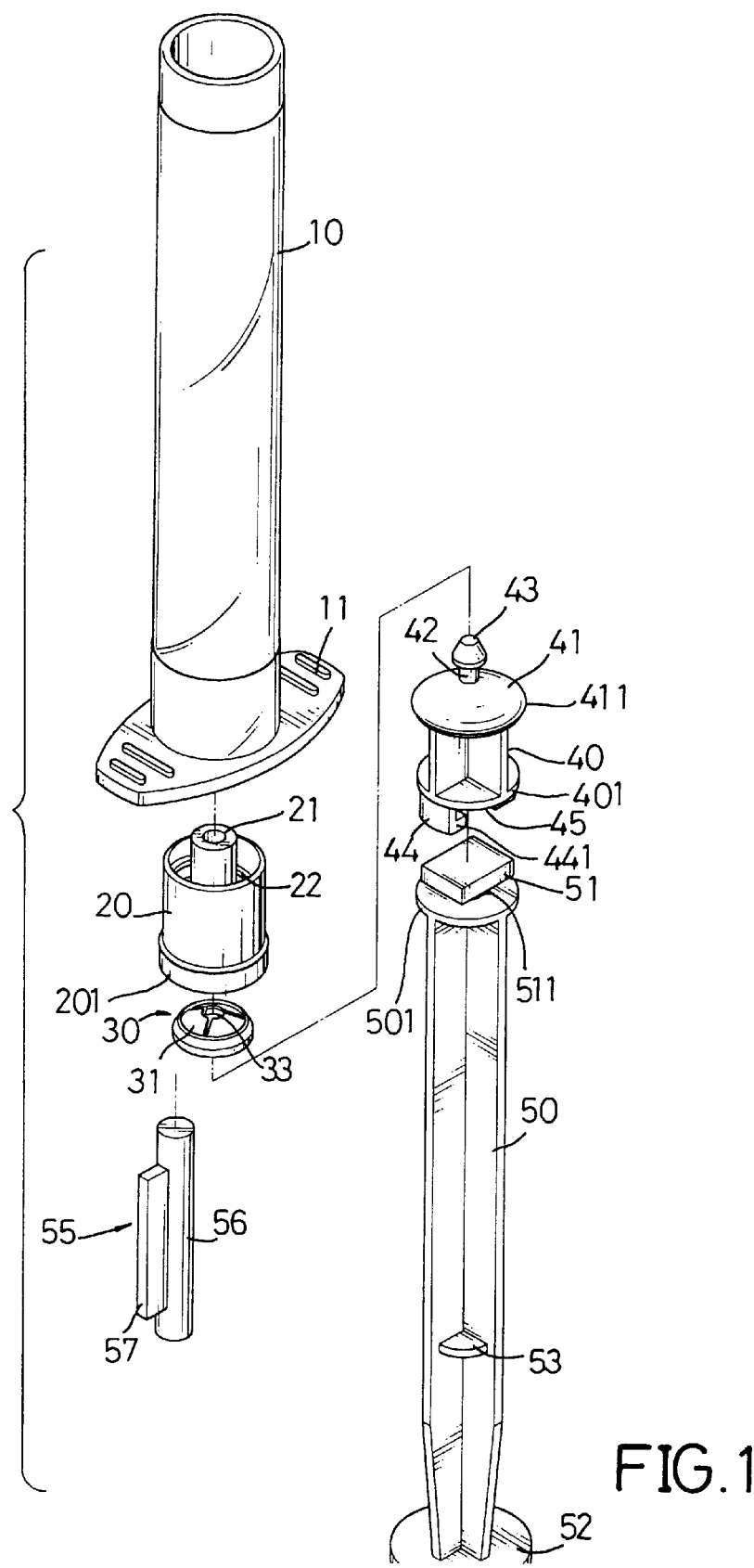
FIG. 1 is an exploded perspective view of the preferred embodiment of the invention.

Shown in FIG. 1 is the preferred embodiment of the invention, a safety hypodermic syringe. The syringe includes a barrel (10), a needle seat (20) airtightly contained in the barrel (10), an elastic ring (30) contained in the needle seat (20), a stopper (40), and a plunger (50) coupled with the stopper (40).

Still with reference to FIG. 1 and together with reference to FIG. 2, the barrel (10) has a lower end round which a finger flange (11) is formed, and an upper end whose diameter is smaller than that of the barrel (10) thus forming a stage (12) in the barrel (10). The barrel (10) has an inner flange (13) formed near the lower end thereof. The function of the stage (12) and the inner flange (13) will be described hereinafter.

The needle seat (20) is a tube like body having a lower end flange (201). The needle seat (20) is able to be inserted in the barrel (10) from the lower end of the barrel (10) and pushed upward until the lower end flange (201) meet and is blocked by the stage (12) in the barrel (10). An inner surface of the needle seat (20) is defined with a female thread which is able to threadedly engage with a male thread or a pair of opposite small protrusions formed on a needle hub (23) of a needle (24). An inner pipe (21) is formed in the needle seat (20) through which medical fluid can flow. An inner circular groove (26) is defined in the needle seat (20) near the lower end thereof.

The ring (30) is made of elastic material that has a certain rigidity, and has at least one, in this embodiment, two, pair of opposite integral plates (31) extending inward and upward to an axis of the ring (30). Each pair of the two opposite plates (31) does not meet one another thus forming a central hollow (33) therebetween. The ring (30) is able to be placed in the inner circular groove (26) of the needle seat (20) before the needle seat (20) is inserted into the barrel (10).

Figure 6:
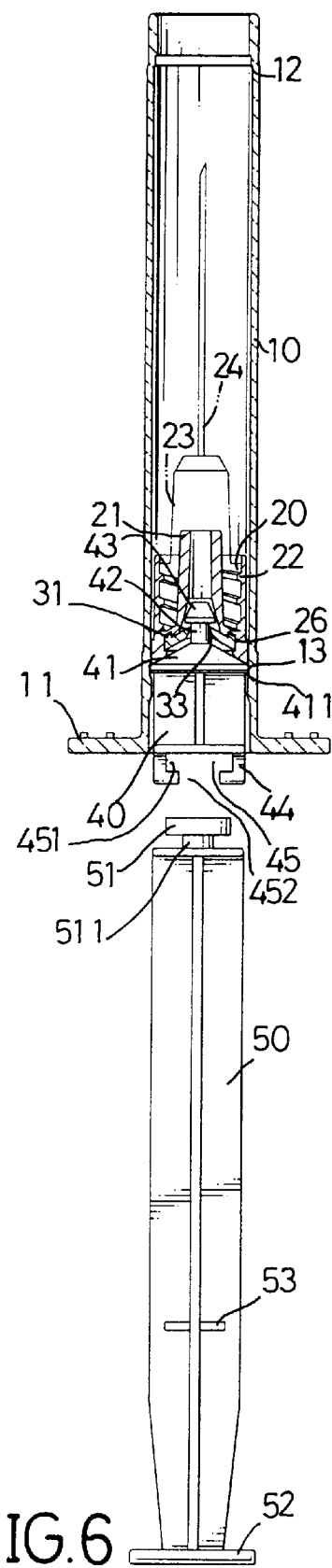

The stopper (40) has a body on which a bottom board (401) and a top cap (41) are formed. The cap (41) has a certain elasticity and when the stopper (40) is inserted into the barrel (10), the cap (41) is able to be airtightly and slidably received by the barrel (10). A central pole (42) is formed on the cap (41) and extends upward. A head (43) whose diameter is a little larger than that of the central pole (42) is formed on a top of the central pole (42). A pair of opposite legs (44) is formed on the bottom board (46) with a foot (441) of each leg (44) being curved and extending to a center of the bottom board (401). As shown in FIG. 6, a T-shaped receiver (45) is thus defined between the two legs (44) having a horizontal portion (451) and a vertical portion (452).

The plunger (50) has a bottom thumb rest (52) and a top board (501) on a center of which a neck (511) is formed. An enlarged plunger head (51) is formed on the neck (511). A small middle disc (53) is formed on the plunger (50) whose function will be described hereinafter.

A security bar (55) is provided having a longer bar (56) and a shorter bar (57) longitudinally formed on the longer bar (56).

In assembly, the ring (30) can be first placed in the inner circular groove (26) of the needle seat (20). Then the needle seat (20) is inserted in the barrel (10) and is pushed upward until the lower end flange (201) thereof meets and is blocked by the stage (12) of the barrel (10). At this time, the needle seat (20) airtightly engages with the barrel (10) with a certain friction force therebetween. Then the plunger head (51) can be inserted sideway into the T-shaped receiver (45) with the plunger head (51) being received in the horizontal portion (451) and the neck (511) being received in the vertical portion (452). The plunger (50) is inserted into the barrel (10) with the stopper (40) entering first. Before the plunger (50) is inserted down to a bottom of the barrel (10), the security bar (55) can be placed between the middle disc (53) and a top surface of the thumb rest (52). Then the plunger (50) is continually pushed until a top end of the shorter bar (57) meets and is blocked by a bottom surface of the thumb rest (52). At this time, the head (43) of the stopper (40) is just able to meet the plates (31) of the ring (30). Finally, the needle hub (23) of the needle (24) is threadedly engaged with the needle seat (20). An assembled syringe is as shown in FIG. 2.

In use, as shown in FIG. 3, the needle (24) can be inserted into a bottle containing medical liquid and then the plunger (50) is pulled backward. The medical liquid can be sucked into the barrel (10). Meanwhile, the security bar (55) falls out which indicates the syringe has been used.

Figure 4:
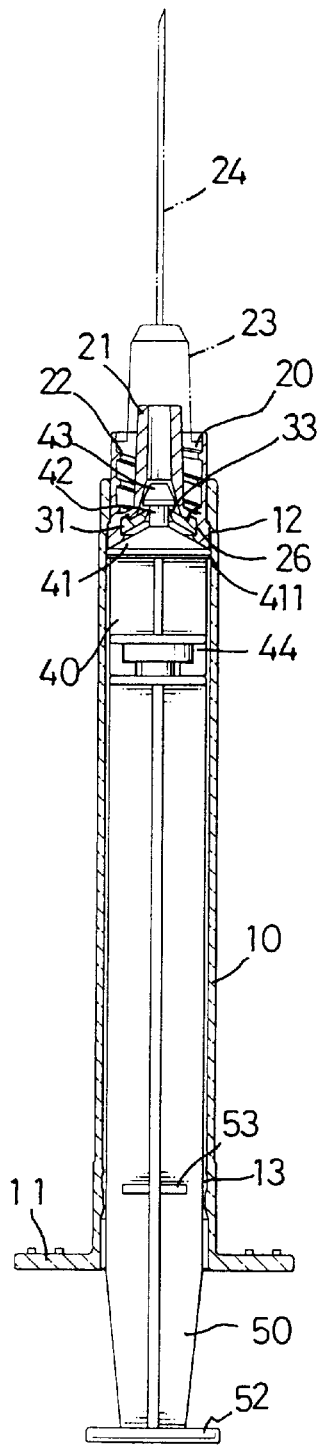

With reference to FIG. 4, by pushing the plunger (50) upward with respect to the barrel (10), the medical liquid contained in the barrel (10) will be driven out from the needle (24) to implement an injection treatment. The plunger (50) is then continually pushed until the head (43) passes through the central hollow (33) and the two pairs of plates (31) fall back on the central pole (42) under the elasticity thereof after the head (43) has passed thereby. It is seen that remaining space in the barrel (10) after the injection treatment has been completed is very small. Therefore, it is understood that there must be relatively less remaining medical liquid in the syringe of the invention.

Figure 5:
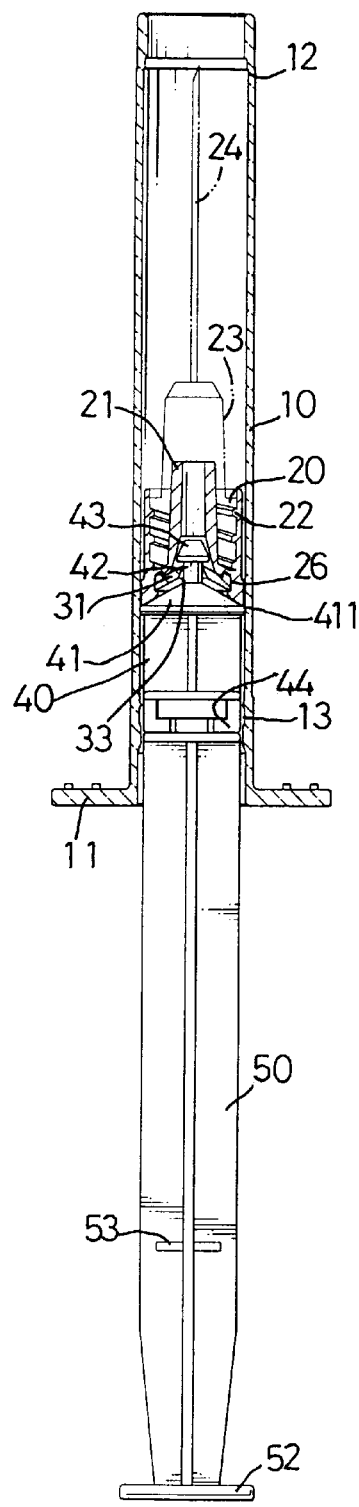

As shown in FIG. 5, when the plunger (50) is pulled back after the injection treatment, the head (43) drives the plates (31), and consequently the needle seat (20), also moves backward.

As shown in FIG. 6, the backward pulling of the plunger (50) finally causes a periphery (411) of the cap (41) to meet and be blocked by the inner flange (13). At this time, a bottom surface of the bottom board (401) is just a little lower than the bottom surface of the thumb rest (11). The plunger (50) can be pushed sideways to slide out from the receiver (45), and the stopper (40), together with the needle (24) threadedly engaging with the needle seat (20), is left in the barrel. The plunger (50) can be recycled and the needle (24) contained in the barrel (10), without a plunger connected therewith which is easily pushed by accident, will not stick out from the barrel (10) again.

Figure 7:
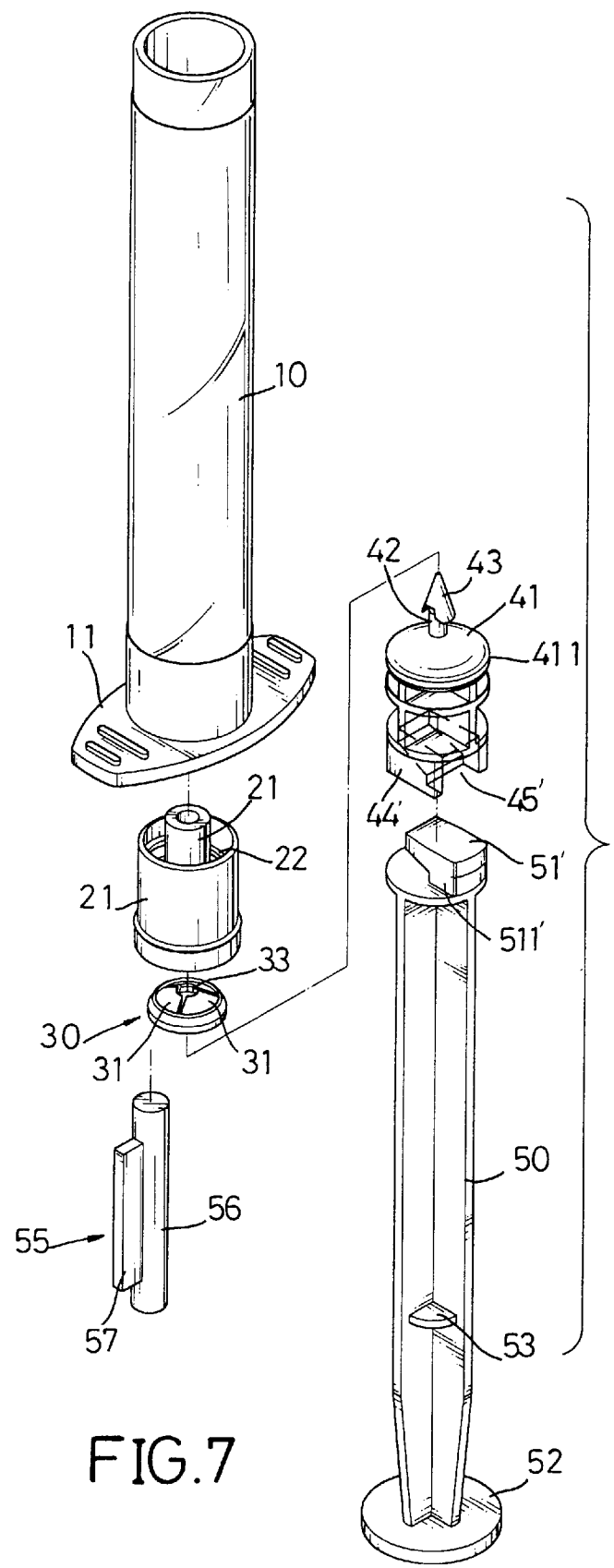
FIG. 7 is an exploded perspective view of another embodiment of the invention.
Figure 8:
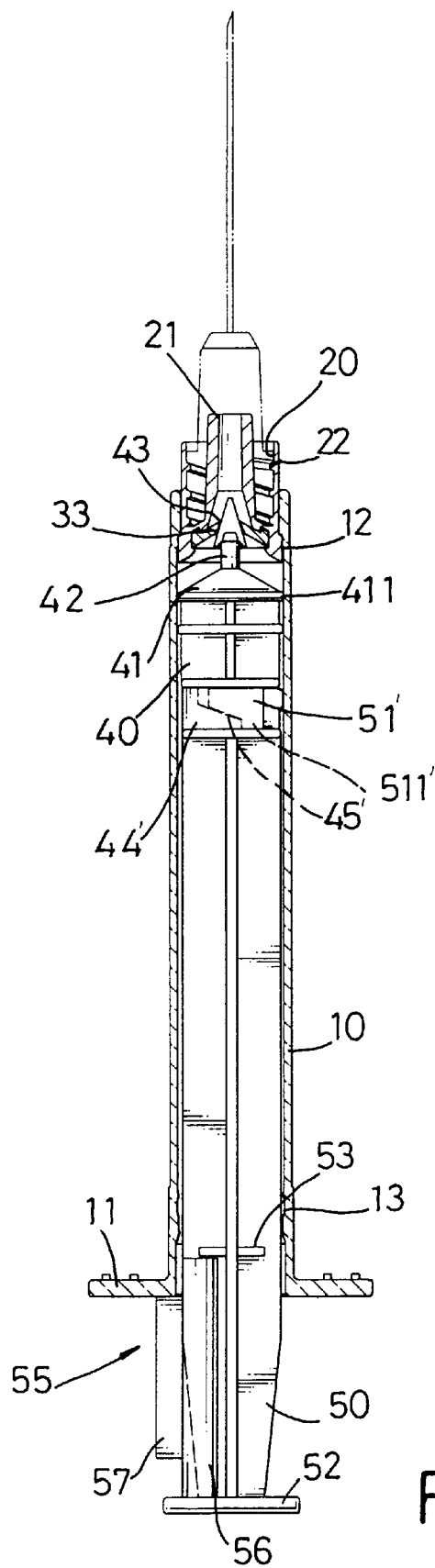
FIG. 8 is a cross sectional view of the embodiment shown in FIG. 7.
Figure 9:
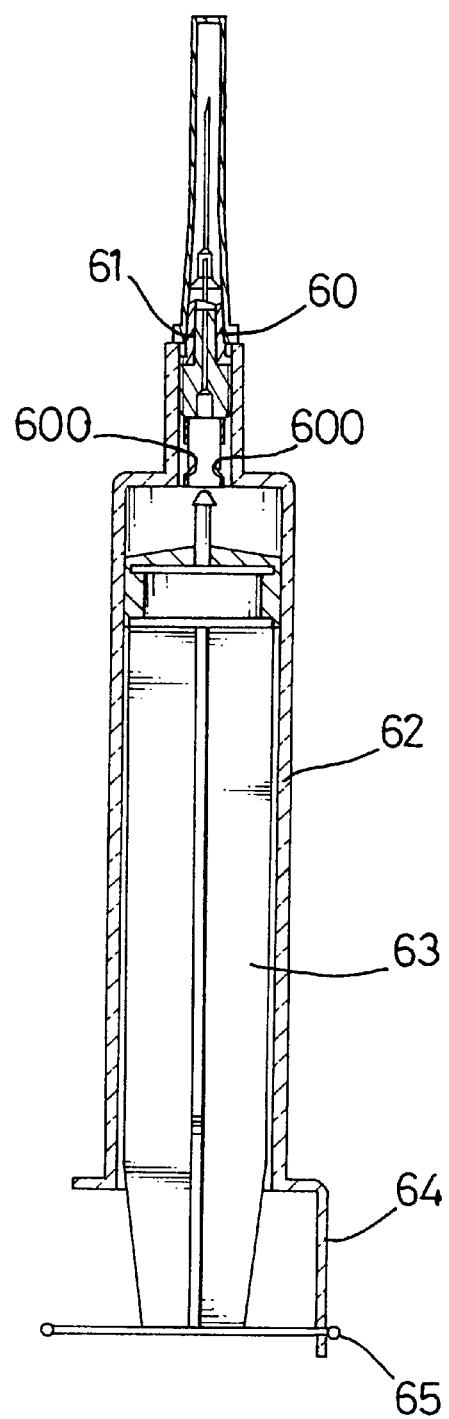
FIG. 9 is a cross sectional view of a conventional safety hypodermic syringe.

Shown in FIGS. 7 and 8 is another embodiment of the invention. In this embodiment, there is only one leg (44') and a foot curved and extending substantially perpendicular to the leg (44'), forming an L-shaped receiver (45'). The neck (511') is formed on one side of a top surface of the top board (501) and the plunger head (51') extends towards an opposite side.

From above description, it could be understood that with the syringe of the invention, the plunger thereof is recyclable, the needle hub thereof is able to be securely installed, the needle thereof is not able to stick out from the barrel thereof after use, remain medicine therein after use is less than conventional syringes, and whether it has been used is able to be plainly indicated by the security bar.

It is to be understood, however, that even though numerous characteristics and advantages of the present invention have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. A safety hypodermic syringe having a barrel, a needle seat airtightly contained in the barrel, a stopper (40), and a plunger (50) coupled with the stopper (40), wherein the improvements comprising:

the needle seat being tube-like and having a central pipe contained therein through which medical fluid can flow, an inner surface of the needle seat provided with a female thread threadedly engageable with a male thread or a pair of opposite small protrusions formed on a needle hub of a needle, an inner circular groove defined in the needle seat near the lower end thereof;

a ring placed in the inner circular groove of the needle seat and made of elastic material having a certain rigidity, the ring having one pair of opposite integral plates extending inward and upward to an axis of the ring, the plates not meeting one another thus forming a central hollow therebetween;

the stopper having a body on which a bottom board and a top cap are formed, the cap having a central pole formed thereon, the central pole having an enlarged head formed thereon, a leg having a foot extending substantially perpendicular to the leg being formed on the bottom board thus forming an L-shaped receiver therewithin which is able to receive a head of the plunger;

the plunger having a bottom thumb rest, a middle disc, and a top board on which a neck is formed, a plunger head being formed on the neck; and, a security bar having a longer bar and a shorter bar longitudinally formed on the longer bar;

wherein before use the plunger head is put into the receiver and the security bar is placed between the middle disc and a top surface of the thumb rest with a top end of the shorter bar pressing against a bottom surface of the thumb rest in order to position the head of the stopper just under the central hollow of the ring and to indicate that the syringe has not been used; and wherein after use the security bar separates from the syringe and the plunger is able to be pulled back out of the barrel and separate from the stopper with the head thereof being removed from the receiver.

2. The syringe as claimed in claim 1, wherein the barrel has an upper end whose diameter is smaller than that of the barrel to form a stage at which a lower end flange of the needle seat is stopped.

3. The syringe as claimed in claim 2, wherein the barrel has a lower inner flange at which a periphery of the cap is able to be stopped when the plunger is pulled back after the syringe has been used.

4. The syringe as claimed in claim 1, wherein a pair of opposite legs is formed on the bottom board, each leg with a foot thereof being curved and extending to a center of the bottom board thus forming a T-shaped receiver therebetween; wherein the neck of the plunger is formed at a center of the top board with an enlarged plunger head formed thereon; and wherein the plunger head and the neck are receiveable in the receiver.

* * * * *